US011459484B2

(12) United States Patent
Kidwell et al.

(10) Patent No.: US 11,459,484 B2
(45) Date of Patent: Oct. 4, 2022

(54) CHEMISTRIES FOR BIOCOMPATIBLE ADDITIVE NANOLITHOGRAPHY

(71) Applicant: The Government of the United States of America, as represented by the Secretary of the Navy, Arlington, VA (US)

(72) Inventors: David A. Kidwell, Alexandria, VA (US); Thomas O'Shaughnessy, Arlington, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 319 days.

(21) Appl. No.: 16/860,426

(22) Filed: Apr. 28, 2020

(65) Prior Publication Data

US 2020/0347267 A1    Nov. 5, 2020

Related U.S. Application Data

(60) Provisional application No. 62/841,016, filed on Apr. 30, 2019.

(51) Int. Cl.
| | | |
|---|---|---|
| *C09D 183/04* | (2006.01) | |
| *C03C 17/32* | (2006.01) | |
| *C09D 133/08* | (2006.01) | |
| *C12M 1/12* | (2006.01) | |
| *G03F 7/20* | (2006.01) | |
| *C08G 77/442* | (2006.01) | |
| *C09D 143/04* | (2006.01) | |
| *C09D 183/10* | (2006.01) | |
| *C12M 1/00* | (2006.01) | |
| *C03C 17/30* | (2006.01) | |

(52) U.S. Cl.
CPC ............ *C09D 183/04* (2013.01); *C03C 17/32* (2013.01); *C09D 133/08* (2013.01); *C12M 25/14* (2013.01); *G03F 7/70058* (2013.01); *C03C 2218/32* (2013.01)

(58) Field of Classification Search
None
See application file for complete search history.

(56) References Cited

U.S. PATENT DOCUMENTS

| | | | |
|---|---|---|---|
| 3,284,425 A | 11/1966 | Gunter | |
| 8,470,264 B2 | 6/2013 | Angros | |
| 2015/0010999 A1* | 1/2015 | Caracci | B05D 3/0254 435/396 |

OTHER PUBLICATIONS

Abdel-Aal et al., Journal of Peptide Science, vol. 22, pp. 360-367 (Year: 2016).*

(Continued)

*Primary Examiner* — Ramsey Zacharia
(74) *Attorney, Agent, or Firm* — US Naval Research Laboratory; Roy Roberts (57) ABSTRACT

A mixed acrylate-siloxane polymer can be used to create three-dimensional (3D) structures of arbitrary shape via nanolithography. Treatment of such structures with amine (such as diamine) makes them permissive for neuronal cell adhesion and growth without need of additional modification such as poly-lysine (D or L) nor laminin.

7 Claims, 5 Drawing Sheets

(56) References Cited

OTHER PUBLICATIONS

Kristan S. Worthington, Luke A. Wiley, Emily E. Kaalberg, Malia M. Collins, Robert F. Mullins, Edwin M. Stone, Budd A. Tucker, and Stephen A. Wynn, "Two-photon polymerization for production of human iPSC derived retinal cell grafts", Acta Biomater, 55 (2017) 385-395. doi:10.1016/j.actbio.2017.03.039.

Hong Chen, Lin Yuan, Wei Song, Zhongkui Wu, Dan Li, "Biocompatible polymer materials: Role of protein-surface interactions," Progress in Polymer Science, vol. 33, Issue 11, 2008, pp. 1059-1087.

Benny Meng Kiat Tong and Shunsuke Chiba, "Diamine-Catalyzed Conjugate Addition to Acrylate Derivatives," Organic Letters 2011 13 (11), 2948-2951.

* cited by examiner

CHEMISTRIES FOR BIOCOMPATIBLE ADDITIVE NANOLITHOGRAPHY

CROSS-REFERENCE TO RELATED APPLICATIONS

This application claims the benefit of U.S. Provisional Application 62/841,016 filed on Apr. 30, 2019, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 110685.

BACKGROUND

On-demand printing of 3D structures of arbitrary shape is sparking a design revolution by empowering the researcher with additional degrees of freedom in experimental design. One of the most popular techniques to achieve sub-micron writing is two-photon lithography. In two-photon lithography a laser is focused through optics immersed in a photosensitive polymer bath to write and make layer-by-layer structures with submicron resolution. Indeed, 3D tools have already received attention in the biological community; nanolithographic scaffolding has been used to encapsulate and direct biological growth and develop 3D micro-scale implants.

For biological studies with neuronal cells, one may wish to constrain neuronal growth to specific areas while directing axonal and dendritic growth over/near electrodes to perform both stimulation and measurements of action potentials. Additive nanolithography can be performed with a number of polymers; SU-8, IP-DIP, and OrmoComp® are amongst the most commonly used. SU-8 is an epoxy polymer, but its refractive index is not as well matched to the optics of the Nanoscribe (Nanoscribe GmbH) tool, reducing the possible print resolution. IP-DIP and OrmoComp® are both acrylate-based polymers, with OrmoComp® being a mixed acrylate-siloxane polymer. IP-DIP is a less rigid polymer compared to OrmoComp® however the UV sensitizer that allows photo-crosslinking of IP-DIP fluoresces in the visible spectrum and subsequently interferes with visualization of fluorescently stained cells on the final structures. Therefore, OrmoComp® may be preferred.

Biological studies using cell culture is a well-established field and it is known that neurons do not adhere well to untreated glass or plastic. Instead, the substrate is typically prepared for seeding with cells by modification with poly-L-lysine or poly-D-lysine (PDL), to introduce a positive charge and increase the initial cell adhesion, and laminin to influence cell differentiation, migration, and also improve adhesion. The cost of these reagents and the time required for their application are not inconsequential, but their application had been deemed necessary to make surfaces permissible for cell culture experiments. Importantly, treatment with PDL-laminin is a bulk coating, meaning the whole substrate or device surface is covered with the same chemistry and cells therefore can grow anywhere on the surface. If one desired to control the locations of cells on a PDL-laminin coated surface the architecture of the underlying substrate would need to influence cell adhesion or the surface would need to be patterned such that the PDL-laminin coating was excluded from specific areas. Either solution introduces significant complexity to the experimental design.

A need exists for alternatives to bulk coatings in order to render polymers (such as OrmoComp®) permissible for neuron adhesion and growth.

BRIEF SUMMARY

A mixed acrylate-siloxane polymer can be used to create three-dimensional (3D) structures of arbitrary shape via nanolithography. Treatment of such structures with diamine renders them permissive for neuronal cell adhesion and growth without need for additional modification such as poly-lysine (D or L) (to introduce a positive charge and increase the initial cell adhesion) or laminin (to influence cell differentiation, migration, and also improve adhesion).

In one embodiment, a structure for cellular growth includes a substrate; and an acrylate-containing polymer attached thereto and in a state of having been functionalized using an amine so as to provide free amine groups on the polymer, wherein the structure is suitable for the growth of mammalian cells thereon. In further embodiments, the substrate is silicon-based (for example, glass), and/or the amine is a diamine.

In another embodiment, a method of preparing a structure for cell culture includes providing an acrylate polymer attached to a substrate, optionally treating the polymer to remove residual solvent and/or monomer; and then performing Michael addition of a an amine with free acrylate groups on the polymer.

BRIEF DESCRIPTION OF THE DRAWINGS

FIG. 1A shows neuronal cell culture showing poor cell adhesion and almost no neurite extension to the OrmoComp® structure written with the Nanoscribe. In FIG. 1B, the neuronal cells were cultured with PDL-laminin coating both the OrmoComp® structure and surrounding glass substrate, with cell adhesion and neurite extension essentially equal across both surfaces. FIG. 1C shows neuronal cell culture on an OrmoComp® structure reacted with 1,3-propane diamine showing improved cell adhesion, in the form of higher cell density, and increased neurite extension and complexity relative to the PDL-laminin treated structure. There is little cell adhesion on the surrounding glass substrate in this case even though the entire surface was exposed to the same chemistry.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Aspects of this work are described in Kidwell et al., "Chemistries for Making Additive Nanolithography in OrmoComp Permissive for Cell Adhesion and Growth," *ACS Appl. Mater. Interfaces* 2019, 11, 22, 19793-19798, which, along with its Supplemental Information, is incorporated herein by reference for the purposes of describing techniques for making, testing, and using the treated polymers described herein.

It was found that treatment of polymers with diamine allows cell growth without the need for pretreatment of the surface with poly-D-Lysine nor laminin (PDL-Laminin). A typical pretreatment uses both of these, and is time-consuming and expensive. Poly-D-Lysine is an adherence factor and laminin is an expensive material typically used as a growth enhancer. PDL-Laminin coatings are typically done immediately before addition of living cells and can take hours to accomplish. The surface treatment described herein can be done weeks in advance of usage, and may be effective much longer (for example months or even one or more years). In further embodiments, the treated material can be either sterilized immediately (and stored in sterile condition) or optionally sterilized after storage but before use.

This system is selective—encouraging cell growth only where the treated polymer is present and thus, allowing patterns of cells to be prepared or to direct growth. Patterning of cells can serve numerous purposes, such as for creation of artificial organs. Because PDL-Laminin coatings can coat areas without polymer present, thus allowing cells to grow uncontrolled, avoiding the use of such coating can be advantageous in preparing structures for controlled growth.

Also contemplated herein is chemistry to further pattern the coating optically, thus further enhancing cell patterning. Amine-containing surfaces produced as described herein can be protected with amine-reactive functionality that is photo-cleavable. Then, one can selectively apply light to remove the protection from desired areas. Suitable chemistry for such photo deprotection is described in Cheng et al., "Photosensitive Chitosan to Control Cell Attachment," *J. Colloid Interface Sci.* 2011, 361(1), 71-78; Wang et al., "A Photo-Sensitive Protecting Group for Amines Based on Coumarin Chemistry," *Chem. Pharm. Bull.* 1997, 45(4), 715-718; and Bhatnagar et al. "Multiplexed Protein Patterns on a Photosensitive Hydrophilic Polymer," *Matrix. Adv. Mater.* 2010, 22(11), 1242-12.

Two patents of note relate to derivatizing polymers with diamines: Lee H. Angros, "Analytic Substrate Coating Method", U.S. Pat. No. 8,470,264 B2 and Günter Schröder and Klaus Tessmar, "Conversion of polymethacrylate to polymethacrylimide in an aqueous system" U.S. Pat. No. 3,284,425. However, it is not expected that these methodologies would actually work for growth of cells. Too high of an amine content (as would be made by the above referenced patents) causes cell death. This was observed in systems such that if the reaction was carried out for too long a period or caused too much amine to be present, the cells died. Prior art typically involves conventional chemistry to form an amide from the ester groups on the polymer chain. Temperature, heat and time are used to place a large number of amines on these chains. The inventive approach described herein is more mild and involves a Michael addition of $\alpha,\beta$ unsaturated esters that preferably reacts with free acrylate functionalities and little with the esters present to put a controlled amount of amines on the polymer chain.

It should be noted that this approach works with photopolymerized acrylate precursors as these have the most "dangling" acrylates present. Acrylates are almost completely absent in commercially produced polyacrylates unless they are cross-linked with a multifunctional acrylate. Commercially-produced plastics could need to be modified to practice the invention. This could be conveniently accomplished by intentionally grafting an acrylate molecule onto the surface. This is frequently done to covalently attach polymers to a surface using an acrylic silane and done on a large scale to make glass-reinforced plastics. An example is in Worthington et al., "Two-photon polymerization for production of human iPSC derived retinal cell grafts", *Acta Biomater,* 55 (2017) 385-395. doi:10.1016/j.actbio.2017.03.039.

EXAMPLES

Figure 1A:
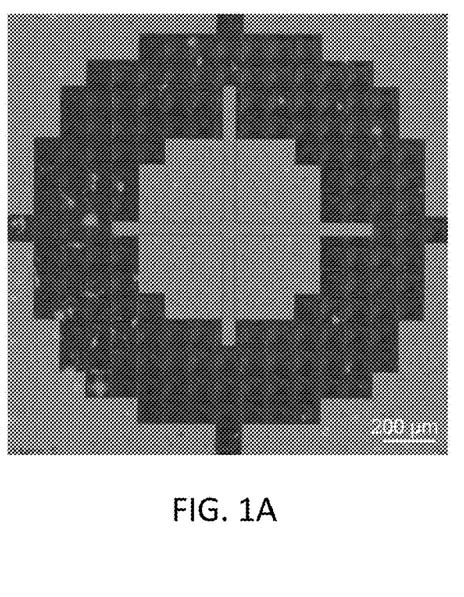
FIGS. 1A-1C are fluorescent images of neuronal cells on two-photon 3D written ring structures. These fluorescent images are falsely colored to represent the green emission of the calcein-AM dye.
Figure 1B:
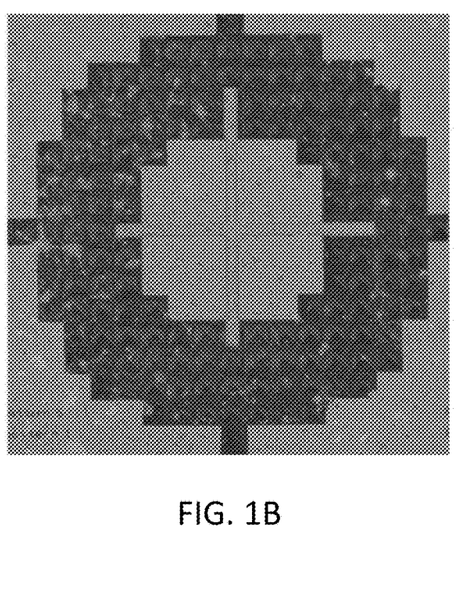
Figure 1C:
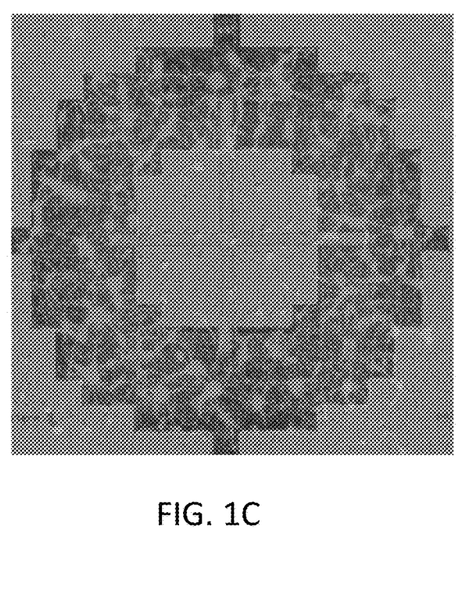

A Nanoscribe (Nanoscribe GmbH) tool was used to build structures of OrmoComp®, a mixed acrylate-siloxane polymer, via two-photon 3D nanolithography. There was little adhesion of E18 murine cortical neurons to the bare OrmoComp® structures (FIG. 1A). Treatment of the OrmoComp® structure with PDL-laminin allowed for neuronal cell adhesion and growth, however growth was not limited to the OrmoComp® structures, but also occurred on the surrounding glass substrate (FIG. 1B). However, by performing a Michael addition with 1,3 propane diamine, the OrmoComp® structures were rendered permissive for neuronal cell adhesion and growth with no additional PDL-laminin treatment (FIG. 1C). Furthermore, cell adhesion was limited to the OrmoComp® structures with more adherent cells and more robust neurite outgrowth than either PDL-laminin treated OrmoComp® structures or glass substrates.

Figure 2A:
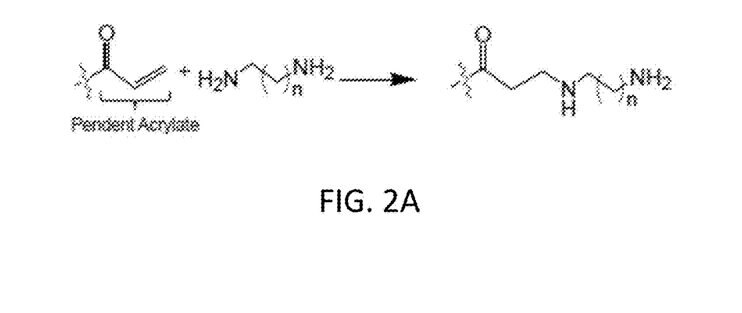
FIGS. 2A-2C illustrate potential reactions of diamines with acrylate groups in a polymer such as OrmoComp®.
Figure 2B:
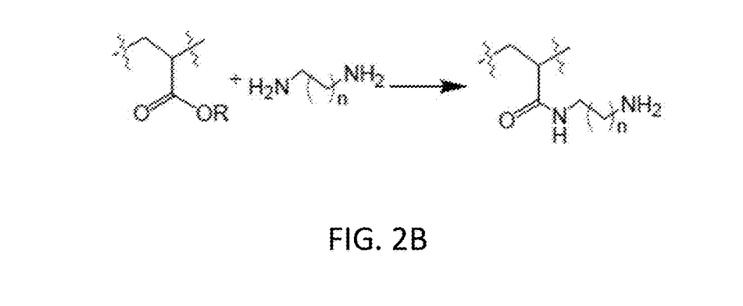
Figure 2C:
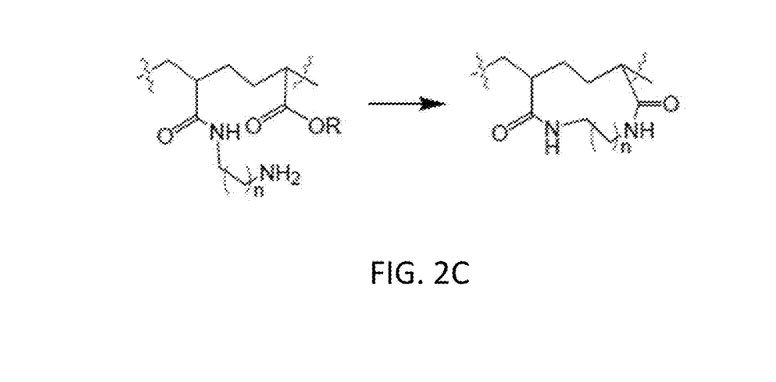

Michael addition of $\alpha,\beta$ unsaturated carbonyls and esters are common reactions that link a nucleophile to the $\beta$ carbon. Under the appropriate conditions and moderate temperature, a primary or secondary amine can undergo Michael addition. In this example, diamines reacted with OrmoComp's® free acrylate groups to provide a surface that would enhance cellular adhesion and growth (FIG. 2A). The reaction is conducted at room temperature to reduce side reactions considered to be detrimental, including nucleophilic attack on an ester producing a primary amine and an amide (FIG. 2B) and cyclization of the primary amine with a nearby ester to produce two amides (FIG. 2C).

With this chemistry, selective growth of neurons on OrmoComp® occurred (FIG. 1C). Importantly, this biocompatibility was achieved without PDL-laminin treatment. It instead mimics that coating by presenting amine groups as the pendent surface chemistry after modification.

Figure 3:
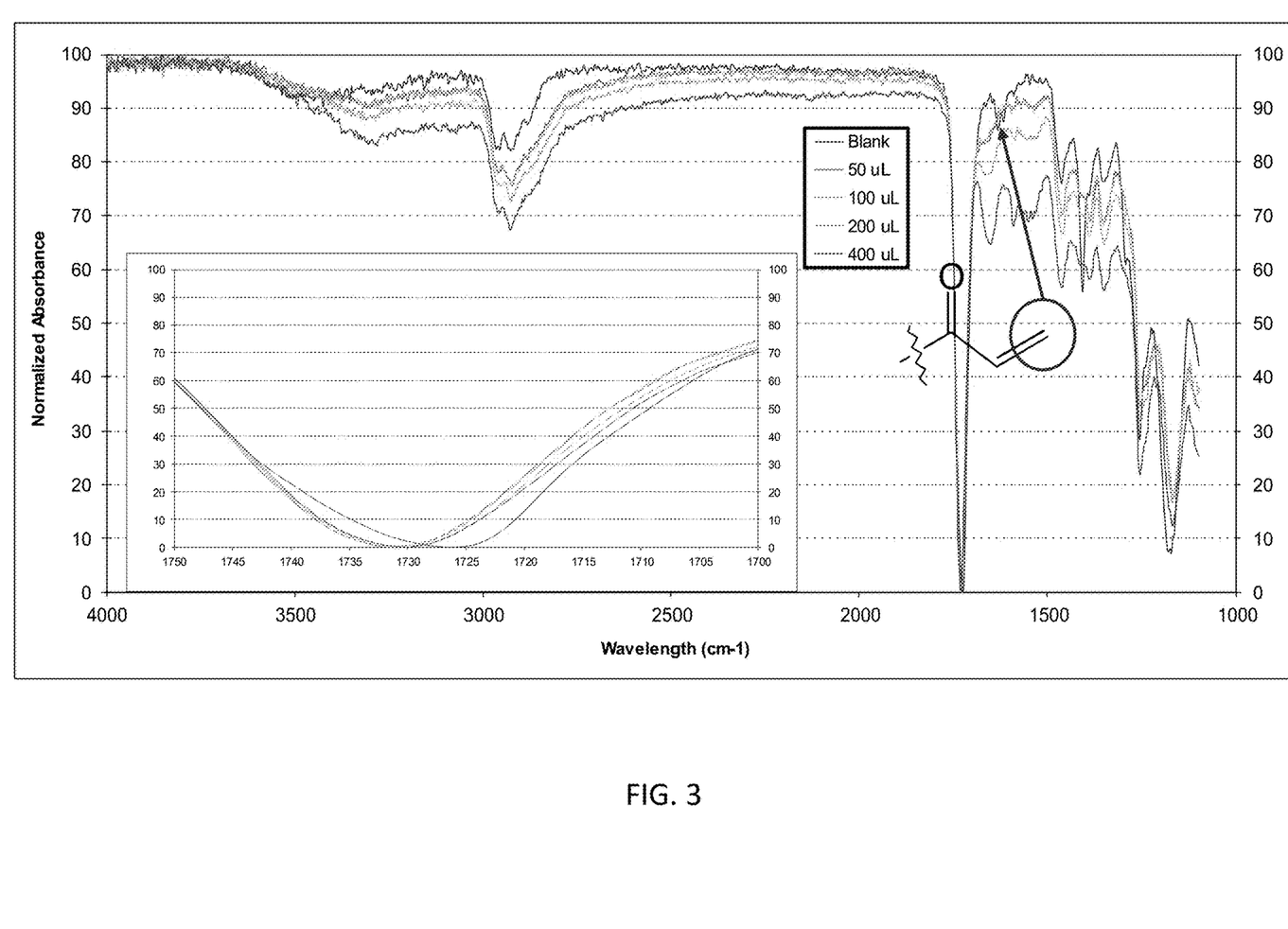
FIG. 3 provides a Fourier-transform infrared spectroscopic (FTIR) analysis of OrmoComp® structures reacted with 1,2 ethane diamine (EDA).

To better understand this chemical modification and its influence on cell culture experiments, it became necessary to make many more OrmoComp® structures. To overcome the throughput limitations of two-photon nanolithography, more conventional photolithography was conducted: Ormo-Comp® was spin coated on glass coverslips and cross-linked under UV illumination. FIG. 3 provides a Fourier-transform infrared spectroscopic (FTIR) analysis of OrmoComp® structures reacted with 1,2 ethane diamine (EDA). The blank shows the expected stretching of an acrylate functionality (1560 cm$^{-1}$) that decreases upon reaction with increasing amounts of EDA. The inset shows the shift of the ester bands from 1725 cm$^{-1}$ to 1731 cm$^{-1}$ after the reaction. The cause of this reproducible shift in the peak maximum is unknown. This peak is characteristic of ester stretching vibrations. However, the ester groups on the rest of the polymer chain should not be affected by the residual acrylate groups.

After reaction with diamine, the acrylate groups are removed and the surface becomes positively charged; this mimics a surface coated with poly-lysine, presenting a pendent amine group, which enhances cell adhesion. The diamine treatment works with a number of different molecules spanning from ethane diamine to hexane diamine. There appeared to be little difference between modified surfaces in terms of overall neuron growth and axon or dendrite extension. The treatment is a covalent modification and robust was evidenced by strong cell growth for up to two weeks as tested in the cell culture experiments.

Figure 4:
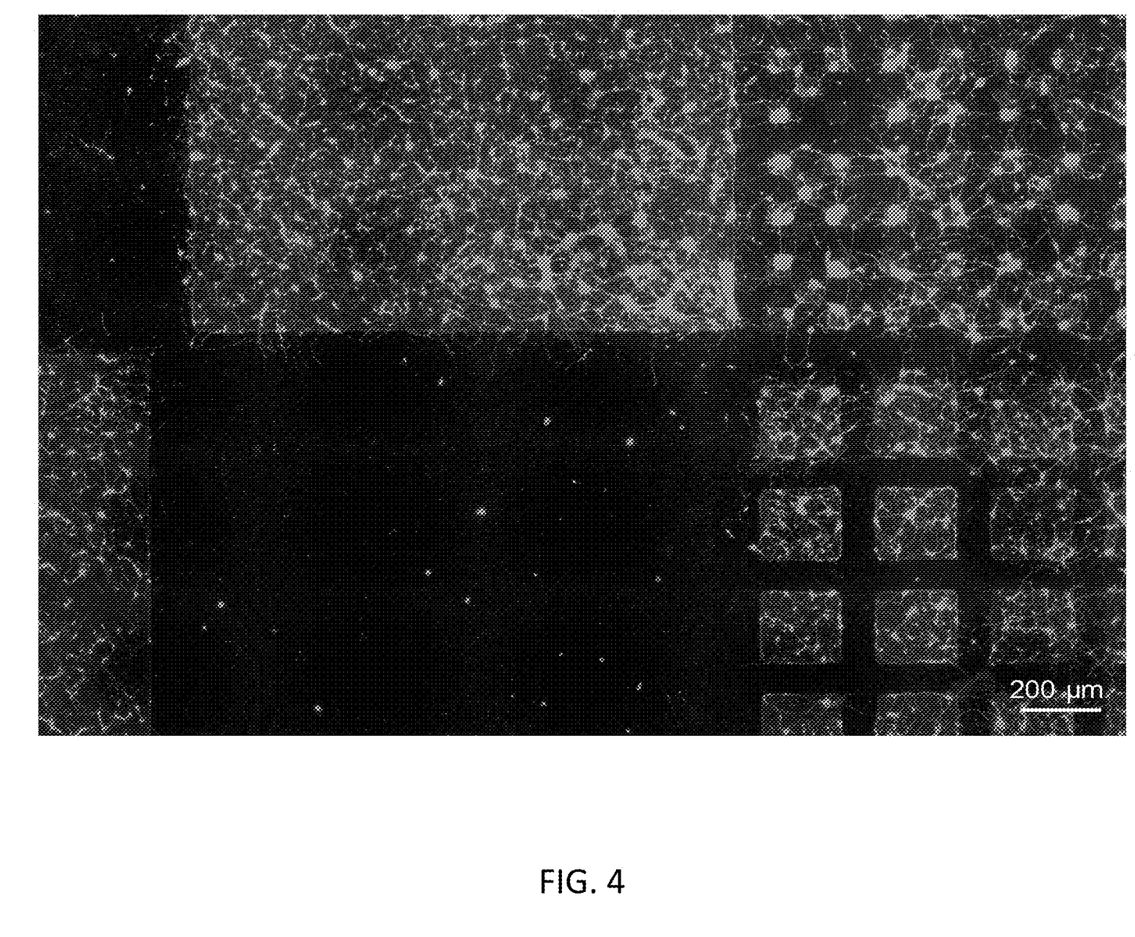
FIG. 4 is a fluorescent image of orthogonal neuronal cell culture on EDA-modified OrmoComp® pads.

That the diamine modification treatment renders OrmoComp® permissive for cell growth is but one advantage offered for designing advanced biological experiments. Importantly, the chemical modification of OrmoComp® occurs in deference to the glass substrate upon which the arbitrary architecture is written. FIG. 4 demonstrates the directed growth of the neuronal cells on OrmoComp® structures and not the surrounding glass substrate. A shadow mask with varying pad dimensions was used to define squares of three different dimensions. Fluorescent image of cells grown on modified EDA OrmoComp® pads. The substrate was photolithographically patterned with 2800 μm, 200 μm, and 100 μm squares. Note the differential growth of neurons on the treated polymer pads compared to the surrounding glass areas. Because PDL-Laminin is not needed to grow cells on these surfaces, the glass being untreated, has no cell adherence or growth. The slightly varying background is an artifact of the stitching process used in gathering the high-resolution images.

Figure 5A:
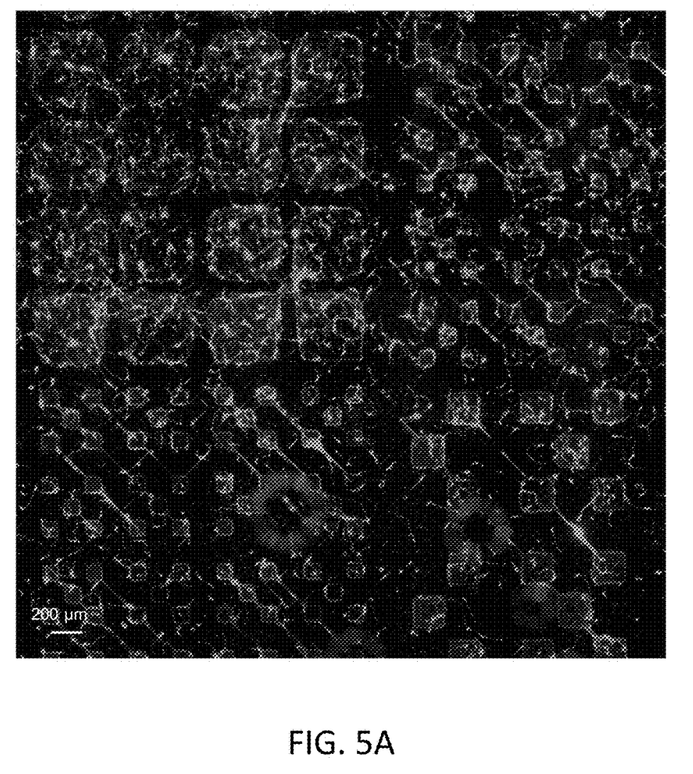
FIGS. 5A and 5B show directed growth of neuronal cells along pad interconnection.
Figure 5B:
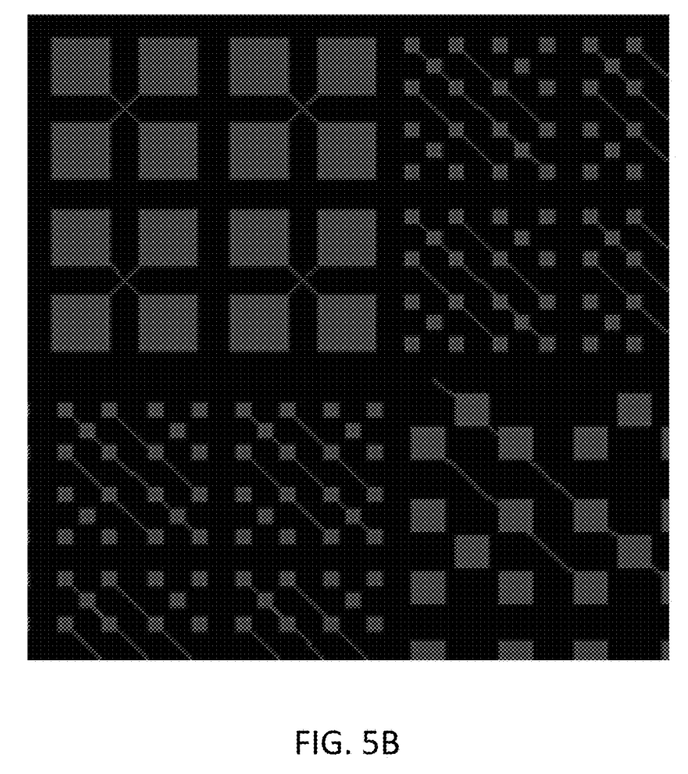

The neurons prefer the chemically modified OrmoComp® surface showing strong growth on all structures. Additionally, diamine treatment may help direct growth and extension along lithographically defined structures. FIGS. 5A and 5B show a close up view of an OrmoComp® surface with 5 μm lines connecting the individual pads. In the fluorescence image, neurons are clearly extending along the connecting lines. There is little growth on the glass surface and the neurons appear to develop axons and dendrites along some of the polymer traces between pads. FIG. 5B shows the portion of the photomask used in patterning the polymer pads corresponding to the area in FIG. 5A.

Furthermore, the orthogonal derivatization of the substrate can be extended to chemistries attached specifically to the glass substrate. Starting with a modified OrmoComp® substrate, subsequent treatment of the surface was with a fluorinated silane, thereby coating the glass areas. XPS data of that surface evidenced fluorine on both the glass areas and modified OrmoComp® pads but this did not appear to inhibit neuronal cell growth. Alternatively, the surface can be treated with a fluorinated anhydride and react only with the polymer and not the glass surface, which blocks the amines but not the glass surface and stops neuronal attachment Advantages The described system improves biocompatibility of an acrylate-siloxane polymer-based material while also eliminating the need for treatment with poly-lysine, laminin, or the like. This technique results in pendent amine groups, mimicking classical cell culture surface preparations. Importantly, the treatment is flexible allowing the researcher the ability to control the number and type of diamine attached to the 3D polymer structure. Significantly, the treatment is an orthogonal modification meaning the polymer surface and surround glass substrate can be modified in deference to each other. Thus, this approach empowers the modern biological research with several new tools for advanced study in cell culture experiments.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Kristan S. Worthington, Luke A. Wiley, Emily E. Kaalberg, Malia M. Collins, Robert F. Mullins, Edwin M. Stone, Budd A. Tucker, and Stephen A. Wynn, "Two-photon polymerization for production of human iPSC derived retinal cell grafts", *Acta Biomater,* 55 (2017) 385-395. doi:10.1016/j.actbio.2017.03.039.

Hong Chena, Lin Yuana, Wei Song, Zhong kui Wu, and Dan Li, "Biocompatible polymer materials: Role of protein—surface interactions", *Progress in Polymer Science,* 33 (2008) 1059-1087.

What is claimed is:

1. A structure for cellular growth comprising:
a substrate; and
an acrylate-containing polymer attached thereto and in a state of having been functionalized using an amine so as to provide free amine groups on the polymer,
wherein the structure is suitable for the growth of mammalian cells thereon, and
wherein at least a portion of the free amine groups are protected by a photo-cleavable functionality.

2. The structure of claim 1, wherein said acrylate-containing polymer is an acrylate-siloxane polymer.

3. The structure of claim 1, wherein said amine is a diamine.

4. The structure of claim 3, wherein said diamine is selected from the group consisting of 1,2-ethane diamine; 1,3-propane diamine; 1,4-butane diamine; and 1,6-hexane diamine.

5. The structure of claim 1, wherein said substrate is glass.

6. A structure for cellular growth comprising:
a glass substrate; and
an acrylate-containing polymer attached thereto and in a state of having been functionalized using a diamine so as to provide free amine groups on the polymer,
wherein the structure is suitable for the growth of mammalian cells thereon, and
wherein at least a portion of the free amine groups are protected by a photo-cleavable functionality.

7. The structure of claim 6, wherein said diamine is selected from the group consisting of 1,2-ethane diamine; 1,3-propane diamine; 1,4-butane diamine; and 1,6-hexane diamine.

\* \* \* \* \*